(12) United States Patent
Masumura

(10) Patent No.: US 9,891,176 B2
(45) Date of Patent: Feb. 13, 2018

(54) LIGHTING DEVICE FOR INSPECTION AND INSPECTION SYSTEM

(71) Applicant: MACHINE VISION LIGHTING INC., Tokyo (JP)

(72) Inventor: Shigeki Masumura, Tokyo (JP)

(73) Assignee: Machine Vision Lighting Inc., Tokyo (JP)

( * ) Notice: Subject to any disclaimer, the term of this patent is extended or adjusted under 35 U.S.C. 154(b) by 0 days.

(21) Appl. No.: 15/308,001

(22) PCT Filed: Aug. 4, 2015

(86) PCT No.: PCT/JP2015/072022
§ 371 (c)(1),
(2) Date: Oct. 31, 2016

(87) PCT Pub. No.: WO2016/151877
PCT Pub. Date: Sep. 29, 2016

(65) Prior Publication Data
US 2017/0067835 A1    Mar. 9, 2017

(30) Foreign Application Priority Data

Mar. 23, 2015 (JP) .................................. 2015-060049

(51) Int. Cl.
*G01N 21/00* (2006.01)
*G01N 21/88* (2006.01)
(Continued)

(52) U.S. Cl.
CPC .......... *G01N 21/8806* (2013.01); *G02B 27/30* (2013.01); *G01N 2201/062* (2013.01);
(Continued)

(58) Field of Classification Search
CPC .. G01N 21/9501; G01N 21/956; G01N 21/88; G01N 21/8803; G01N 21/953;
(Continued)

(56) References Cited

U.S. PATENT DOCUMENTS 9,494,422 B2 * 11/2016 Masumura ............. G01B 11/30
9,638,641 B2 *  5/2017 Masumura ......... G01N 21/8806
(Continued)

FOREIGN PATENT DOCUMENTS

JP  2010-261839 A  11/2010
JP  2013-120099 A   6/2013

OTHER PUBLICATIONS

Office Action from priority application.

*Primary Examiner* — Hoa Pham
(74) *Attorney, Agent, or Firm* — Dilworth & Barrese, LLP

(57) ABSTRACT

In the inspection lighting device, between a surface light source for emitting an inspection light and the inspection object, at least one shielding mask is disposed, and a lens is disposed on a side closer to the inspection object than the shielding mask such that the shielding mask is positioned across the focus position of this lens as a center. In an irradiation solid angle of the inspection light for the inspection object formed when the light emitted from the surface light source is irradiated on to the inspection object by the lens the shielding mask forms a dark area. So that, in accordance with a change in reflection, transmission, scattering occurring at a feature point on the inspection object, a shape, a size, a tilt of the irradiation solid angle of the inspection light can be changed.

10 Claims, 6 Drawing Sheets

(51) Int. Cl.
*G02B 27/30* (2006.01)
*G02B 27/14* (2006.01)
*G02B 27/02* (2006.01)

(52) U.S. Cl.
CPC ............... *G01N 2201/068* (2013.01); *G01N 2201/0636* (2013.01); *G01N 2201/0638* (2013.01); *G02B 27/02* (2013.01); *G02B 27/144* (2013.01)

(58) Field of Classification Search
CPC ........ G01N 21/95; G01B 11/30; G01B 11/24; G01B 11/306
USPC ........................................... 356/237.1–237.5
See application file for complete search history.

(56) References Cited

U.S. PATENT DOCUMENTS

| | | | | |
|---|---|---|---|---|
| 2009/0237677 | A1* | 9/2009 | Aoki | G01B 11/12 356/602 |
| 2010/0182589 | A1* | 7/2010 | Hirose | G01J 3/02 356/51 |
| 2011/0272096 | A1* | 11/2011 | Serikawa | G01N 21/956 156/345.24 |
| 2014/0233040 | A1* | 8/2014 | Gergen | G01B 11/0608 356/609 |
| 2014/0355003 | A1 | 12/2014 | Masumura | |
| 2015/0316488 | A1* | 11/2015 | Masumura | G01N 21/8806 356/237.2 |

* cited by examiner outer housing of inspection lighting device is schematically shown by the dotted lines lines representing half mirror 4 in case of arrangement including half mirror,
and imaging device C, inspection object W and optical axis are shown as broken line.

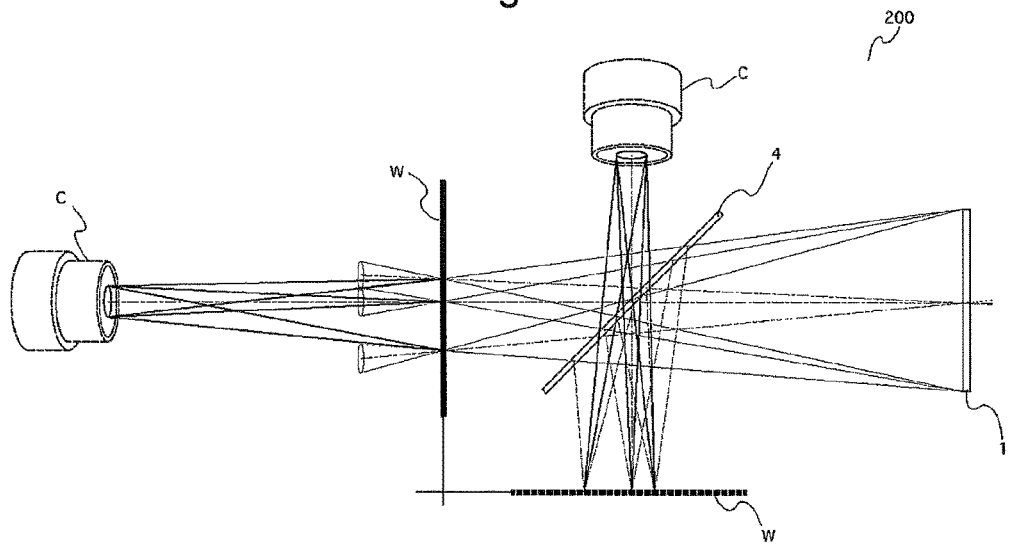

lines representing half mirror 4 in case of arrangement including half mirror, and imaging device C, inspection object W and optical axis are shown as broken lines whereas all observation solid angles are denoted by bold lines.

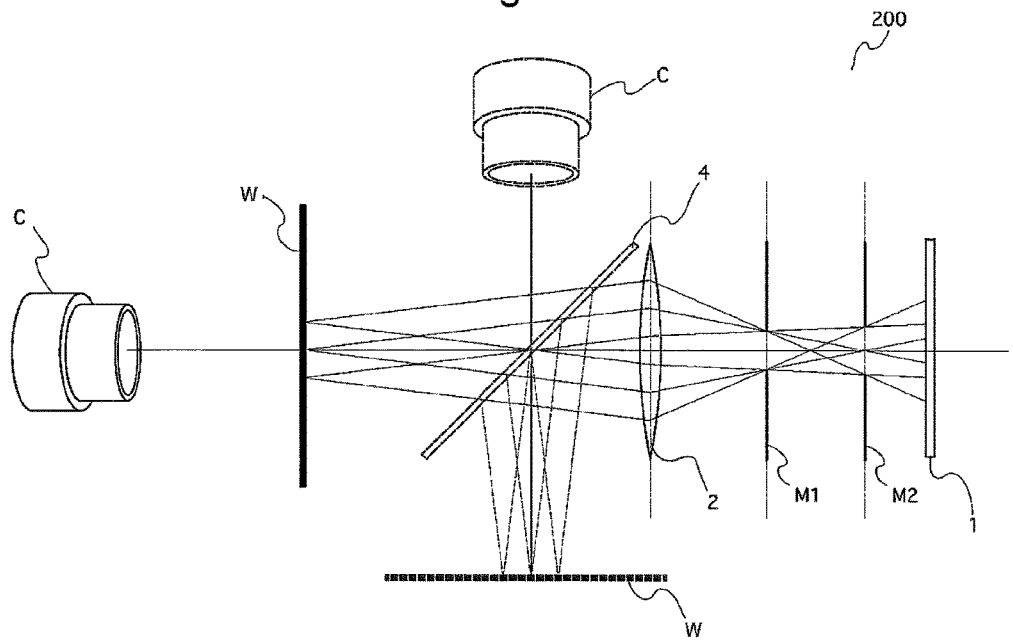

lines representing half mirror 4 in case of arrangement including half mirror, and imaging device C, inspection object W and optical axis are shown as broken lines.

Fig.6

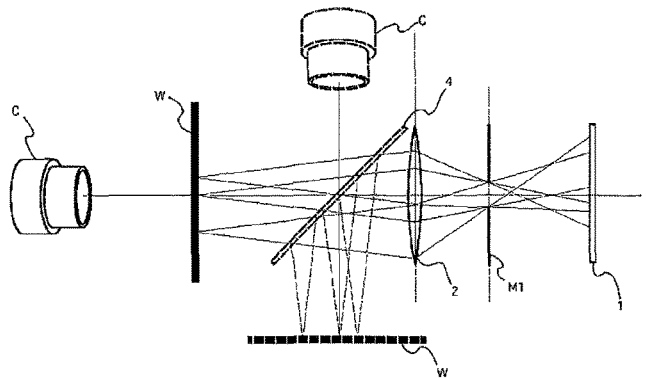

(a) when distance between inspection object and inspection lighting device is long

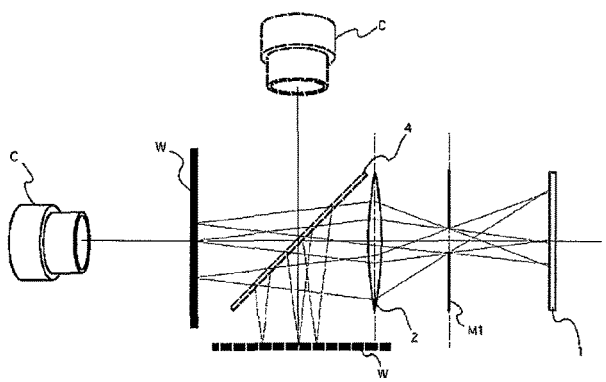

(b) when distance between inspection object and inspection lighting device is medium

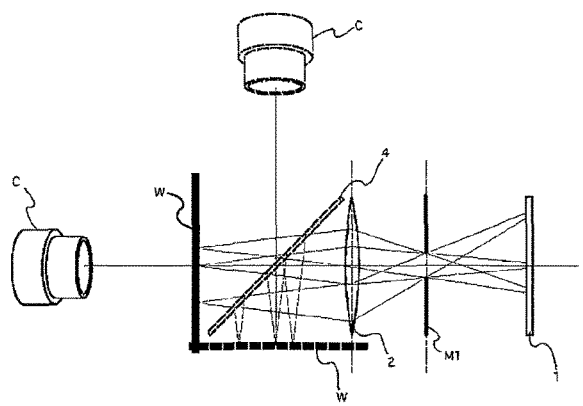

(c) when distance between inspection object and inspection lighting device is short lines representing half mirror 4 in case of arrangement including half mirror, and imaging device C, inspection object W and optical axis are shown as broken lines.

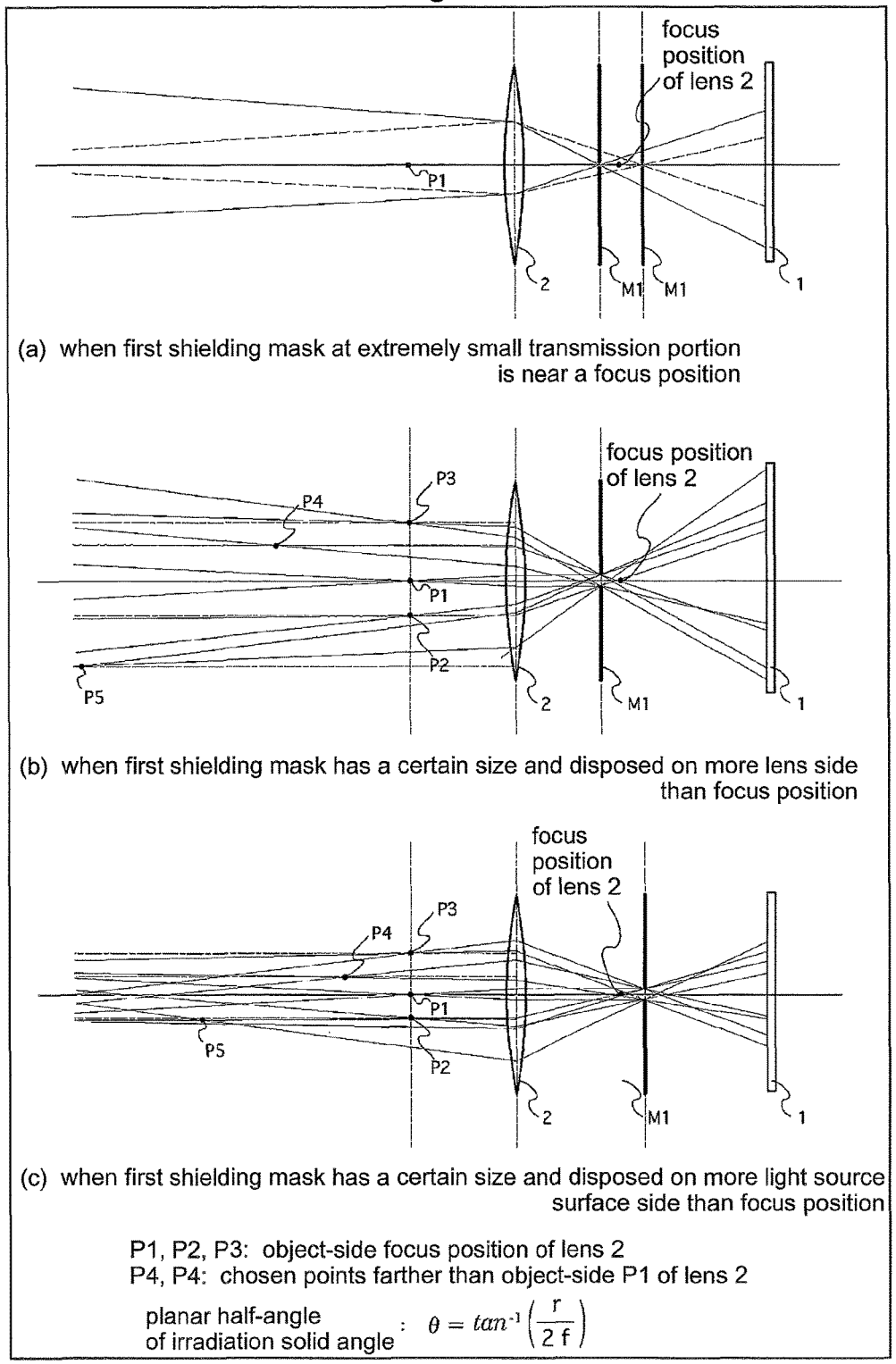

Fig.8
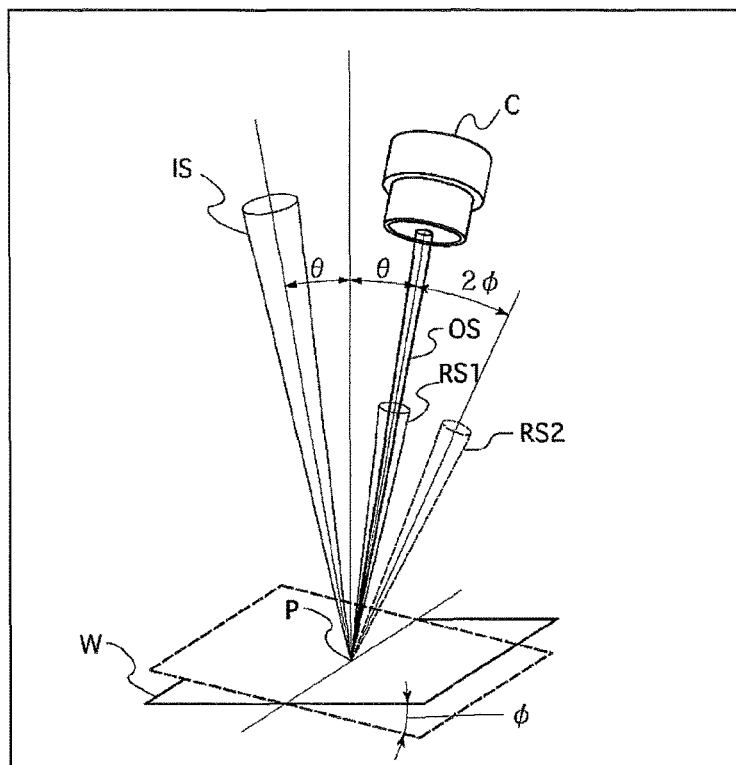
(a) solid angle variation of reflected light due to partial tilt of inspection object
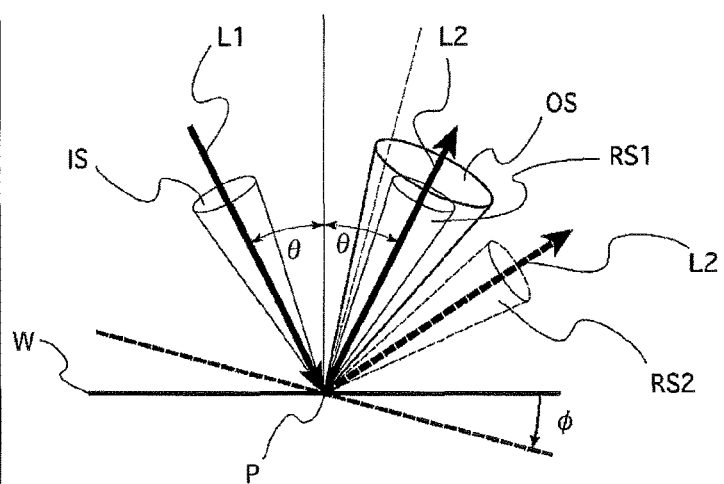
(b) solid angle variation of involution relation between solid angle change of reflected light and observation solid angle

LIGHTING DEVICE FOR INSPECTION AND INSPECTION SYSTEM

TECHNICAL FIELD

The present invention relates to a lighting device for inspection for use in inspecting an appearance, a damage, a defect or the like in a product by e.g. irradiating inspection light onto the product as an inspection object. The invention relates also to an inspection system.

BACKGROUND ART

As an example of such lighting device for inspection for use in e.g. inspection of an appearance of a product, it is possible to cite a coaxial lighting device shown in Patent Document 1, in which an imaging direction is in agreement with a lighting direction for an inspection object. This coaxial lighting device includes a light source configured to emit inspection light in a direction parallel with an inspection object face of the inspection object, and a half mirror disposed with a tilt between the inspection object and an imaging (image pick-up) device disposed upwardly of the inspection object and configured to reflect the inspection light toward the inspection object and to transmit the reflected light from the inspection object toward the side of the imaging device.

Incidentally, in recent years, there is a demand for ability of detecting a feature point such as a defect difficult to detect with using the above-described inspection lighting device through a captured image thereof. More particularly, since the surface property of a product as the inspection object is not a perfect mirror surface, precision control of e.g. an optical axis or shape of an irradiation solid angle for obtaining desired gradation information on a feature point on the inspection object surface is difficult. Thus, even if the inspection light can be irradiated, as there occurs significant contrast variation depending on at what position on the inspection object the feature point is present, identification of the feature point is difficult.

For instance, it is conceivable to increase the inspection precision by limiting the irradiation area of the inspection light to the inspection object only with use of an aperture stop or the like, thereby to decrease stray light which is a reflected light or scattered light from an non-inspection target object.

However, even when reduction of such stray light coming into the imaging device is made possible, in case of a very small defect etc., there occurs significant variation in the brightness of captured image, which makes detection thereof as a defect impossible.

More specifically, even when there occurs a small change in the reflection direction of irradiated inspection light due to presence of e.g. a small defect on the inspection object, if this change is in such a range as confined within an observation solid angle of the imaging device, the brightness of the captured image will remain unchanged, regardless of presence/absence of the defect. Or, if the irradiation solid angle of the inspection light is large and the tilt of its optical axis differs among respective points on the inspection object, a small change in the reflection direction can not be grasped as a change of light amount within the observation solid angle of the imaging device; and moreover, the light amounts within the observation solid angle of the imaging device will vary irregularly for/among the respective points. Consequently, the machine vision is unable to accurately detect such minor defect or the like in the inspection target range.

CITATION LIST

Patent Literature

Patent Document 1: JP 2010-261839 A

SUMMARY OF INVENTION

Technical Problem

The present invention has been made in view of the above-described state of the art. The object of the invention is to provide an inspection system and an inspection lighting device capable of providing a constant amount of change in the light amount within an observation solid angle of an imaging device at respective point within an imaging range of an inspection object, even when a variation of reflection or scattering occurring at a feature point is small so that the feature point such as a defect is very small or irrespective of at what position of the feature point may be present, thereby allowing detection of such small feature point.

Solution to Problem

Namely, the present invention has been made based on a novel technical concept as follows. By rendering a size, a shape, a tilt etc. of its irradiation solid angle of inspection light irradiated from the inspection lighting device uniform and making adjustment thereof possible when desired, even a very small amount of change in its reflection or scattering due to presence of a small defect of the inspection object or the like can be grasped as a corresponding change in a light amount within the observation solid angle of the imaging device and an image comprising such change as contrast information can be obtained.

More particularly, according to the present invention, there is provided an inspection lighting device configured to irradiate inspection light onto an inspection object, the inspection lighting device adapted to an inspection system having an imaging device for imaging light reflected, transmitted or scattered by the inspection object, the inspection lighting device comprising:

a surface light source for emitting an inspection light;

a lens disposed between the surface light source and the inspection object and configured to form an irradiation solid angle for the inspection object by using light emitted from the surface light source as the inspection light to be irradiated onto the inspection object; and a first shielding mask disposed between the surface light source and the lens and disposed before and after a focus position of the lens as a center, the first shielding mask being configured to form the irradiation solid angle of the inspection light irradiated onto respective point on the inspection object by light shielding;

wherein with respect to an observation solid angle for the respective point on the inspection object formed when the imaging device images light from the inspection object, a shape, a size or a tilt of the irradiation solid angle being settable to obtain a desired change in contrast for the respective point.

According to a further characterizing feature of the present invention, the inspection lighting device further comprises a second shielding mask disposed between the first shielding mask and the surface light source and disposed adjacent position image formed for the inspection object by the lens, the second shielding mask being capable of creating an irradiation area, an irradiation shape or an irradiation pattern of the inspection light for the inspection object as desired.

With the inspection system and the inspection lighting device described above, an approximately uniform irradiation solid angle of inspection light irradiated onto respective point on the inspection object can be formed by the lens in cooperation with the first shielding mask, whereas the lens and the second shielding mask cooperate to realize limiting of the irradiation of the inspection light to a needed portion only of the inspection object or also ability to form the inspection light into a desired shape in the irradiation area.

In other words, in case a conventional lighting device having a surface light source is employed for instance, the shape, the tilt of the irradiation solid angle for respective point on the inspection object are determined by the relation between respective point on the inspection object and the shape of the light surface of the lighting device. So, obtaining uniform inspection light is difficult. On the other hand, according to the present invention, the shape, the tilt etc. of the irradiation solid angle for respective point on the inspection object can be rendered uniform, yet adjustable when desired. In addition, by irradiating the inspection light only to a required area, it is possible to prevent stray light from the inspection object.

Moreover, the first shielding mask provides the ability to set appropriately the shape and the angle of the irradiation solid angle of the inspection light to be irradiated onto respective point on the inspection object, in relation to the size, shape and angle of the observation solid angle of the imaging device, thus making it possible to make a small defect or the like to be detected easily or not to be detected at all if needed.

Further, an irradiation solid angle of various configurations can be formed such as a configuration in which only a center portion of the irradiation solid angle at respective point on the inspection object appears as a dark area and its peripheral area only appears as a light area. Also, it is possible to arrange such that imaging of scattered light alone is made possible with preventing reflected light or transmitted light from the inspection object from entering the observation solid angle of the imaging device. In these manners, inspection light can be irradiated with an irradiation solid angle corresponding to a variety of inspection objects or a change in the light occurring at various feature points to be detected.

In the present invention, when an inspection light having approximately uniform irradiation solid angle is irradiated onto the inspection object, regarding a change in the solid angle of the reflected light or transmitted light that occurs when its reflection direction or transmission direction is changed due to presence of a defect or the like, in order to be able to detect such change even though it may be very small, the relation between the irradiation solid angle of the inspection light and the observation solid angle of the imaging device will be adjusted in regard to the shape, angle, size thereof such that a light amount change within the observation solid angle becomes maximum while light amount change for any other change becomes minimal. With this, it becomes possible to grasp such change alone selectively. Therefore, grasping of a small change in light amount due to such minor defect or the like would be difficult with the conventional lighting device in which the shape, angle size of the irradiation solid angle of its inspection light differ for respective point on the inspection object. On the other hand, such detection is made possible with the lighting device provided by the present invention.

In order to realize control to render approximately uniform the size of the irradiation solid angle of inspection light to be irradiated onto respective point on the inspection object and to enable adjustment of tilt distribution of the irradiation solid angle relative to the optical axis center, the first shielding mask can be disposed at a position before/after the focus position of the lens as the center. Namely, by varying the aperture of the first shielding mask, the irradiation solid angle at respective point on the inspection object can be set to a desired shape or size. Further, if the first shielding mask is disposed at the focus position of the lens, this will result in all optical axes of the irradiation solid angles of the inspection light becoming parallel to the optical axis of the inspection light. If the first shielding mask is disposed on more lens side than the focus position of the lens, this will result in the irradiation solid angle of the inspection light being tilted to the direction of widening the inspection light. Whereas, if the first shielding mask is disposed on more outer side than the focus position of the lens, this will result in tilting of the irradiation solid angle of the inspection light to the direction of narrowing the inspection light. In these manners, by varying the layout and its aperture portion of the first shielding mask, various adjustments regarding the irradiation solid angle of the inspection light are made possible which directly affects the solid angle of the reflected light or transmitted light from the inspection object. Consequently, the relative relation between the inspection object and the observation solid angle of the imaging device for observing a reflected light, a transmitted light or a scattered light from the inspection object can be set to a mode suitable for obtaining desired contrast information.

In this way, the ability of obtaining desired contrast information by the inventive inspection lighting device and the inventive inspection system having the inventive lighting device and an imaging device for imaging a light reflected, transmitted or scattered by the inspection object is attributable to the fact as follows. Namely, brightness of respective point on the inspection object is determined by an amount of light of the reflected, transmitted or scattered light from respective point on the inspection object toward the imaging device and this light amount is determined by involution (overlapping) relation between the solid angle of the reflected light, transmitted light or scattered light from respective point on the inspection object and the observation solid angle of the imaging device, and the device or system is provided with the function of adjusting approximately uniform the irradiation solid angle of the inspection light that directly affects the reflected light or transmitted light from respective point on the inspection object.

In order to cause the brightness information of the inspection object imaged by the imaging device to exhibit approximately uniform change throughout its imaging range, it is necessary to maintain substantially fixed the involution relation between the observation solid angle formed on the respective point on the inspection object by the imaging device and the solid angle of the reflected light, transmitted light or scattered light from respective point on the inspection object. This can be realized by rendering the shape and size of the irradiation solid angle of the inspection light approximately uniform by moving the first shielding mask before and after the focus position of the lens as the center and adjusting its tilt angle to conform to the tilt of the observation solid angle at respective point on the inspection object.

Also, in order to allow desired generation of irradiation area, irradiation shape or irradiation pattern of the inspection light for the inspection object, this can be realized by providing the second shielding mask in addition to the first shielding mask and disposing this second shielding mask adjacent the position of image forming on the inspection object by the lens. With this arrangement, it becomes possible to adjust both the irradiation area of the inspection light and its irradiation solid angle independently, while keeping the shape, size and tilt of the irradiation solid angle of the inspection light approximately uniform.

In order to realize easy inspection also of shape precision of the inspection object, this can be realized by using the second shielding mask formed with a predetermined mask pattern, in addition to the first shielding mask and causing this pattern to form an image on the inspection object. With this arrangement, thanks to the approximately uniform irradiation solid angle adjusted by the first shielding mask, contrast information having uniform brightness change can be obtained by the imaging device. And, if there is any problem in the shape of the inspection object, such shape defect can be easily detected since there will occur corresponding distortion in the pattern image obtained by the imaging device as contrast information.

With approximate agreement established in the respects of shape, size and tilt thereof between the solid angle of the reflected light or transmitted light at respective point on the inspection object and the observation solid angle formed at respective point on the inspection object, even when a small feature point is present on the inspection object, this will cause a corresponding change in the involution relation between the solid angle of the reflected or transmitted light and the observation solid angle, so that change in the contrast information corresponding to such minor feature point can be obtained. This can be realized either by an arrangement wherein a half mirror is provided for changing the irradiation direction of the inspection light and also allowing transmission of this inspection light to be image-captured by the imaging device and an optical axis of the irradiation solid angle of the inspection light for respective point on the inspection object is rendered into approximate agreement with an optical axis of the observation solid angle of the imaging device for respective point on the inspection object or by an alternative arrangement wherein the observation solid angle of the imaging device is set along a direction of line-symmetry relative to a normal line drawn to the inspection object relative to the irradiation direction of the inspection light and an optical axis of the solid angle of the reflected light or transmitted light for respective point on the inspection object is rendered into approximate agreement with an optical axis of the observation solid angle of the imaging device for respective point on the inspection object.

Advantageous Effects of Invention

As described above, with the inspection lighting device and inspection system according to the present invention, the size and/or mode etc. of the irradiation solid angle of the inspection light irradiated onto respective point on the inspection object and its dark area can be freely adjusted, whereby the involution relation between the solid angle of reflected, transmitted or scattered light from respective point on the inspection object and the observation solid angle formed at respective point on the inspection object by the imaging device can be set substantially uniform, eventually, even a minor defect or the like which would be difficult to detect with the convention can now be detected.

BRIEF DESCRIPTION OF DRAWINGS

FIG. 4 is a diagram showing the inspection lighting device and the inner structure of the inspection system according to the same embodiment, with the inspection object being set with a tilt, showing also irradiation solid angle at respective point on the inspection object, FIG. 5 is a diagram showing an inspection lighting device for conventional lighting use, a structure of an inspection system and irradiation solid angle at respective point on an inspection object, FIG. 6 is a diagram showing an inspection lighting device according to an embodiment having addition of a second shielding mask, a structure of an inspection system and irradiation solid angle at respective point on the inspection object, FIG. 7 is a diagram showing the inspection lighting device and the structure of the inspection system according to one embodiment of the present invention, showing irradiation solid angle at respective point on the inspection object with the distance device between the device, system and the inspection object as a parameter, and FIG. 8 shows relation among a change in solid angle of reflected light due to a partial tilt of the inspection object, irradiation solid angle and observation solid angle.

DESCRIPTION OF EMBODIMENTS

A first embodiment of the present invention will be explained.

An inspection system 200 including an inspection lighting device 100 and an imaging device C is configured to provide a so-called coaxial lighting arrangement using a half mirror 4 for providing agreement between a direction of imaging an inspection object W and a direction of lighting the inspection object W. In use thereof, a feature point such as a defect present on the inspection object W will appear as a "contrast" in an image captured by the imaging device C. Incidentally, in FIGS. 2 through 5, a case having a half mirror is represented by dotted lines whereas a case having no half mirror is represented by solid line, respectively. Here, the "feature point" such as a defect in the inspection object W is understood to include broadly such defect as a damage, a dent, a distortion on the surface, a defect in shape of appearance, presence/absence of a hole, etc. or any other type of feature.

Figure 1:
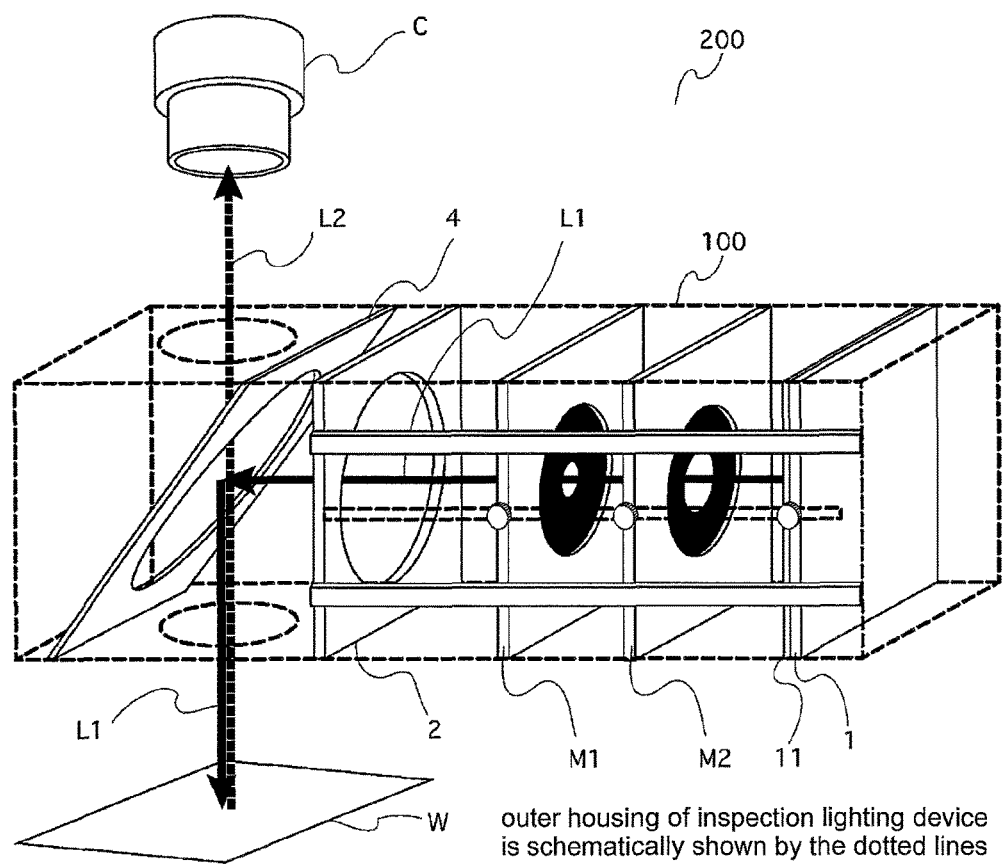
FIG. 1 is a diagrammatic perspective view showing appearance of an inspection lighting device and inspection system relating to one embodiment of the present invention.
Figure 2:
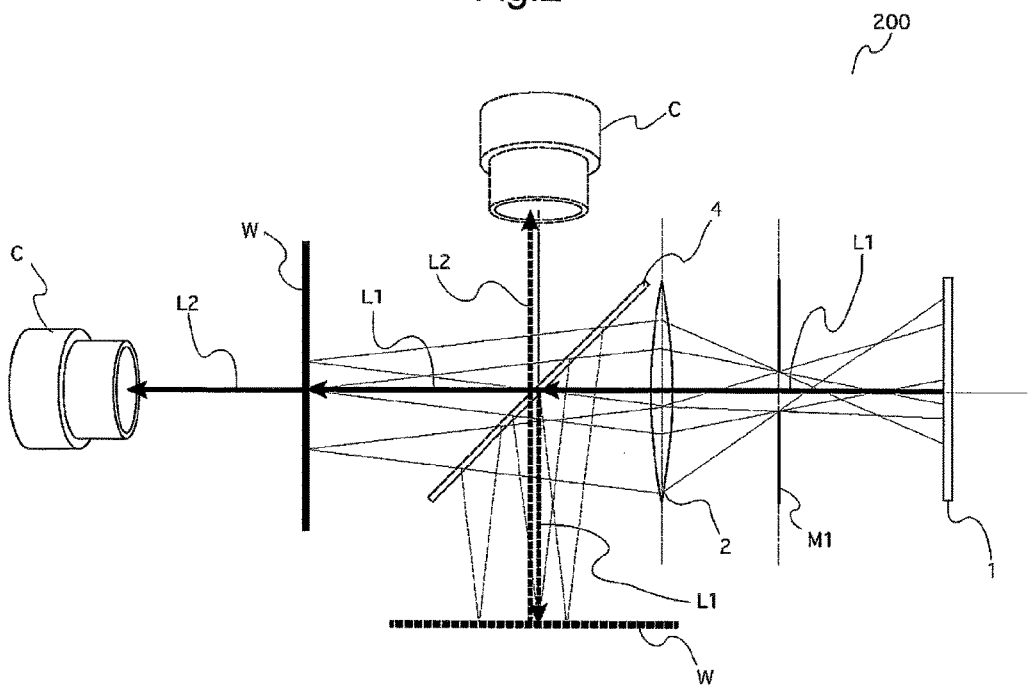
FIG. 2 shows relation among a change in solid angle of a reflected light due to a partial tilt of an inspection object, irradiation solid angle and observation solid angle.
Figure 3:
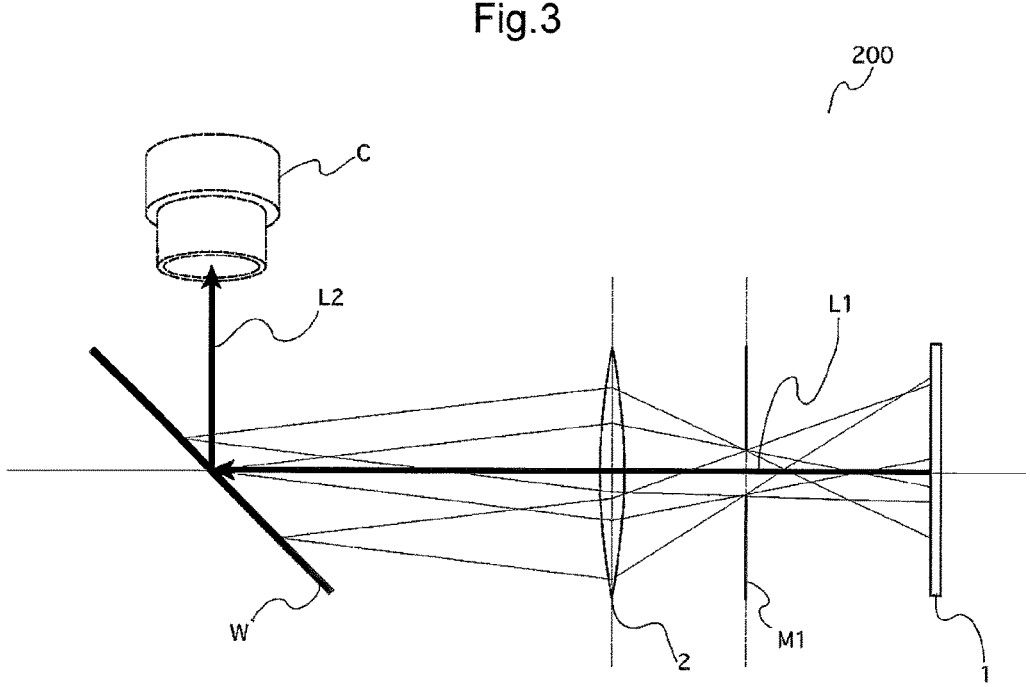
FIG. 3 is a diagram showing the inspection lighting device, the inner structure of the inspection system relating to the same embodiment and irradiation solid angle at respective point on the inspection object.

The inspection lighting device 100, as shown in the perspective view of FIG. 1 and the diagram of FIG. 2, has an approximately tubular housing. Inside this housing, the inspection object W and a portion extending to the imaging device C, there are formed an irradiation light path L1 for irradiating an inspection light from a surface light source 1 onto the inspection object W, and a reflection/transmission light path L2 along which a reflected light or transmitted light from the inspection object W travels to the imaging device C. In case the half mirror 4 is provided, the imaging device C will be mounted to a top opening side of the housing and the inspection object W will be placed on a bottom opening side of the housing.

Incidentally, as shown in FIG. 1 and FIG. 2, in case the half mirror 4 is provided, the irradiation light path L1 will consist of a portion extending from the surface light source 1 to the half mirror 4 and a portion along which the light partially reflected by the half mirror reaches the inspection object. On the other hand, in case the half mirror 4 is not provided, the inspection light will be directly irradiated onto the inspection object along the irradiation light path L1, and in the example shown in FIG. 2, a light path along the transmitted light from the inspection object W to reach the imaging device C will constitute a light path L2.

On the irradiation light path L1, in the order of traveling of the inspection light, there are disposed the surface light source 1 emitting the inspection light, a first shielding mask M1 disposed before/after a focus position of a lens 2 as the center, and the lens 2 configured to form an irradiation solid angle for the inspection object W from the inspection light emitted from the surface light source 1. In case a half mirror is provided, in addition to the above, the half mirror 4 will be disposed with a tilt relative to the reflection/transmission light path L2 and the irradiation light path L1 so as to reflect the inspection light partially downwards. Moreover, in case a second shielding mask for forming an irradiation area of the inspection light is provided, this second shielding mask will be disposed between the surface light source 1 and the first shielding mask and in vicinity of the position image-formed on the inspection object W by the lens 2, and the inspection light will be irradiated onto the inspection object W. However, the specific function of the case of providing the second shielding mask will be explained later with reference to FIG. 4.

Further, on the reflection/transmission light path L2, in the case of providing a half mirror, the half mirror 4 is disposed, so that the reflected light partially transmitted by this half mirror 4 will be observed by the imaging device C. Whereas, in the case of providing no half mirror, in the case of the example shown in FIG. 2, the path along which the transmitted light from the inspection object W travels to reach the imaging device C constitutes the path L2. On this light path L2, no other component than the half mirror 4 is present in the arrangement shown in FIG. 1 and FIG. 2. However, depending on a case, for the purpose of shutting off stray light from the inspection object, a mask, an aperture stop or the like can be disposed for partially shielding the reflected or transmitted light from the inspection object.

Next, layouts, arrangements and functions of the respective components will be described in details.

The surface light source 1 has a light emitting face 11 constituted of a chip type LED, a diffusion plate or the like. Further, this surface light source 1, as shown in FIG. 1, is mounted in such a manner that it can advance or retract along the irradiation light path inside the tubular housing so as to provide ability of adjustment of irradiation starting position for the inspection light. More particularly, independently of control of irradiation solid angle by the first shielding mask M1 and control of irradiation area by a second shielding mask M2 to be described later, it is possible to control degree of uniformity and brightness distribution, etc. of the inspection light on the inspection object W, relative to the path of the inspection light which is determined by position relation among the first shielding mask M1, the second shielding mask M2, the lens 2 and the inspection object W. Since the irradiation light path differs depending on the irradiation area, if the surface light source 1 is preset with a predetermined brightness distribution, emission light wavelength distribution, polarization characteristics distribution, etc., it will become possible for the irradiation area to change such distribution or render it uniform also if desired.

The second shielding mask M2, as shown in FIG. 1, is mounted in such a manner that it can advance or retract along the irradiation light path inside the tubular housing. Then, in accordance with a distance between the lens 2 and the inspection object, the second shielding mask per se can adjust its position near the imaging position for the inspection object. With this arrangement, as shown in FIG. 5, the irradiation light from the surface light source 1 can be partially shielded, and the shape of the aperture of the second shielding mask will be approximately image-formed on the inspection object W. Thus, by varying the shape, the size or the like of the aperture of the second shielding mask M2, the irradiation area of the inspection light on the inspection object W can be changed. Further, this adjustment or change can be carried out independently of the control of irradiation solid angle by the first shielding mask M1 which will be described later.

The first shielding mask M1 is disposed between the lens 2 and the surface light source and at a position before/after the focus position of the lens 2 as the center; and as shown in FIG. 1, the mask M1 is mounted to be movable back and forth along the irradiation light axis inside the housing. If the first shielding mask M1 is disposed at the focus position of the lens 2 for instance, as illustrated in FIG. 2, sizes, shapes and tilts of irradiation solid angles at the respective points on the inspection object W become all the same. This is also true with the case shown in FIG. 3 in which distances between the respective points on the inspection object and the lens 2 differ from each other. Further, this is also true, irrespective of presence/absence of the half mirror 4 or the distance between the inspection object W and the lens 2, as illustrated in FIG. 6.

Next, there will be explained the case wherein the first shielding mask M1 is disposed before/after the focus position of the lens 2.

As shown in FIG. 7 (a), firstly, in case the first shielding mask M1 is disposed near the focus position at a minimal transmitting portion thereof, the irradiation solid angle becomes substantially 0 (zero). In case the first shielding mask M1 is disposed on more lens 2 side than the focus position of the lens 2, the inspection light, as shown by the solid lines in FIG. 7 (a), will be formed as a light path tilted to flare (widen) toward the outer side than the light axis center. Further, in case the first shielding mask M1 is disposed on more surface light source 1 side than the focus position of the lens 2, as shown by the broken lines in FIG. 7 (a), the inspection light will be formed as a light path tilted to converge at the light axis center. On the other hand, the shapes and sizes of the irradiation solid angles of the inspection light for the respective points on the inspection object are uniformly determined by the shape and size of the aperture of the first shielding mask M1, as shown in FIG. 7 (b), FIG. 7 (c). And, independently of this, the tilt of the irradiation solid angle can be controlled by the position of the first shielding mask M1.

P1, P2, P3 in FIG. 7 represent points all located at the distance of the object-side focus position of the lens 2. Light passing at least P1 is only such a light which is caused by the lens 2 to travel along the axis of the light irradiated from the surface light source 1. When the aperture of this light path is caused to have a diameter of (r) for instance by the first shielding mask M1, the irradiation solid angle at this P1 will be uniquely determined by a focal length (f) of the lens 2 and the diameter (r) of the aperture only as shown in the lower section in FIG. 7. Ideally, this is also true with P2, P3 having the same distance as P1 from the lens. Also, at P4, P5 which are arbitrarily chosen points having distances longer than the focal length of the lens 2, the irradiation solid angles thereof will have substantially same shape and size as the irradiation solid angle at P1.

In contrast to the above-described inventive lighting arrangement capable of forming approximately uniform irradiation solid angle, in case of conventional lighting arrangement using only light source surface, as shown in FIG. 4, the irradiation solid angles of the inspection light for respective points on the inspection object W differ in their shapes, sizes and tilts. This is because the irradiation solid angle for respective point on the inspection object W is determined by a projection shape, size and angle of the surface light source 1 as the lighting is viewed in reverse from that point. On the other hand, the observation solid angle at respective point on the inspection object is determined by the relation between the pupil position, pupil shape, pupil size of the imaging device C and the respective point on the inspection object W. The brightness at respective point on the inspection object is determined by involution relation between the solid angle of reflected or transmitted light which directly reflects the irradiation solid angle at respective point and the observation solid angle. If a change occurring in the solid angle of reflected or transmitted light is very small, it becomes difficult to obtain a same amount of change of light at respective points on the inspection area.

In general, the degree of tilt of the observation solid angle other than the principal optical axis is determined by the characteristics of the imaging optical system. And, this varies coaxially from the principal optical axis, due to the properties of standard lens. For such imaging optical system, if it is desired to obtain a uniform change of light, in particular, a uniform change amount of the reflected or transmitted light at respective position of the inspection object relative to such variation of tilt of the solid angle thereof, it is effective to maintain the relation between the irradiation solid angle thereof and the observation solid angle constant at respective point by varying the tilt of the irradiation solid angle of the inspection light for the inspection object coaxially relative to the principal optical axis.

Here, with reference to FIG. 8, there will be explained the involution relation between the irradiation solid angle and the observation solid angle and contrast information obtained by the imaging device.

In FIG. 8 (a), there is contemplated a case wherein an inspection light having an irradiation solid angle IS is irradiated at a point P on the inspection object W, with focus being placed on the point P of the inspection object W. The drawing illustrates how brightness of point P will change when the plane including the point P of the inspection object is tilted partially by φ, more particular how relative relation between solid angles will vary, relative to the observation solid angle OS formed at the point P by the imaging device C, when the solid angle RS1 from the reflected light from the point P changes to a solid angle RS2.

In FIG. 8 (a), the shapes and sizes of the solid angles RS1 and RS2 of the reflected light from the point P are equal to the irradiation solid angle IS of the inspection light for the point P. Further, the tilt of the reflected light solid angle RS1 is a same amount as the tilt (θ) of the irradiation solid angle IS of the inspection object in the direction of line-symmetry of the irradiation solid angle IS of the inspection light relative to the normal line drawn to the point P. In this, if the optical axis of the observation solid angle OS formed by the imaging device C for the point C is in agreement with the optical axis of the solid angle RS1 of the reflected light and also the size of the observation solid angle OS is much smaller than that of the solid angle RS1 of the reflected light, then, the brightness of the point P image-captured by the imaging device C will be rate-limited by this size of the observation solid angle OS, so that the brightness will not change if the solid angle RS1 of the reflected light is tilted within the range in which this convolution relation remains unchanged. However, it is assumed here that optical energies within the solid angles RS1 and RS2 of the reflected light are uniformly distributed within the respective solid angles.

Next, in FIG. 8 (a), there is contemplated a case wherein the plane including the point P of the inspection object W is tilted partially by φ. In this case, the solid angle RS1 of the reflected light from the point P will be tilted by 2φ as shown by RS2 represented by the dotted lines in the drawing. In this, if the solid angle RS2 of reflected light from the point P does not have any involution relation relative to the observation solid angle OS formed by the imaging device C for the point P, the brightness of the point P as seen from the imaging device C will be 0 (zero). Conversely, if the planar half-angle of the irradiation solid angle IS is sufficiently larger than the tilt angle 2φ of the reflected light caused by the partial tilting of the inspection object W, no change will occur in the brightness of the point P. Also, no change in brightness of point P occurs also if the planar half-angle of the observation solid angle OS is greater than a sum of the tilt angle 2φ of the reflected light and the planar half-angle of the solid angle RS1 of the reflected light. These show that brightness of the point P is predetermined eventually by the involution relation between the solid angle RS1 of the reflected light from the point P and the observation solid angle OS for the point P and that change in brightness of point P can be controlled by setting the relation relating to the shapes, sizes and tilts of the irradiation solid angle IS of the inspection light irradiated to the point P and the observation solid angle OS for the point P.

FIG. 8 (b) is a section taken along a plane in (a) including the irradiation optical axis of the inspection light, the normal line to the point P and the reflection optical axis from the point P. From this illustration, the tilts of the respective components and their involution relation can be grasped more quantitatively. It is noted, however, that FIG. 8 (b) illustrates a case in which the observation solid angle OS is greater than the irradiation solid angle IS, namely, the solid angle RS1 of reflected light. In the case the inspection object W is tilted and the solid angle RS1 of the reflected light from the point P is changed to RS2 as denoted by the dotted line, there is no involution relation relative to the observation solid angle OS in this illustrated example, so that the optical energy within this observation solid angle OS becomes 0 (zero). Thus, even if the light contained in this observation solid angle OS is converged again at the point for imaging, the point P still can be visible only as total darkness.

In FIG. 8 (b), if the shape and size of the observation solid angle OS are same as those of the irradiation solid angle IS and its tilt in agreement with that of the solid angle RS1 of the reflected light from the point P, then, if the inspection object W is tilted even by a small amount, there will result at least in corresponding decrease of the overlapping portion between the observation solid angle OS and the reflected light solid angle RS1, so there will occur corresponding change in the brightness of the point P as seen via the observation solid angle OS. Moreover, the smaller the respective solid angle is, the greater the change amount in the brightness of the point P is when the inspection object W is tilted by the same angle. Conversely, the larger the respective solid angle is, the smaller the change amount in the brightness of the point P is when the inspection object W is tilted by the same angle. Further, with appropriate setting of the shape, size, tilt etc. of the irradiation solid angle IS and the observation solid angle OS in accordance with change in the light generated at a desired feature point on the inspection object, precision detection of a feature point which conventionally could not be detected in a stable manner is now made possible. The present invention focused on this principle and arrived at the conception of the inspection lighting device capable of accurate control of the shape, size and tilt of the irradiation solid angle.

The half mirror 4 is circular disc-like component supported to an approximately square-shaped frame member. With use of such half mirror 4, detachment portion of the front face and the back face where reflection or transmission of the half mirror 4 occurs can be formed very thin. Thus, it becomes possible to minimize "ghost" phenomenon due to minute refraction, internal reflection etc. occurring at the time of transmission of reflected light from the inspection object W through the half mirror 4.

The first shielding mask and the second shielding mask can respectively be a conventional aperture stop using a plurality of blades as a commonly employed optical material or can also be a combination of a very thin shielding plate having a desired aperture and an aperture stop or a component of e.g. liquid crystal allowing electronical aperture setting thereof.

Further, as a further embodiment of the aperture of the first shielding mask, this can be an oval or narrow and long slit, rather than an circular aperture. With this arrangement, in detection of a feature point on the inspection object, it is possible to provide its detection sensitivity with anisotropy. Namely, in this case, the irradiation solid angle for respective point on the inspection object is formed as an irradiation solid angle which extends in the same longitudinal direction as the slit of the first shielding mask and which at the same time is very thin in the direction of its short side thereof. In this case, the detection sensitivity for a tilt of the inspection target in the longitudinal direction is low, and the detection sensitivity in the short side direction alone can be set high. In this case, however, the shape, size, tilt of the observation solid angle formed by the imaging device at the respective point on the inspection object needs to be same substantially in compliance with the short-side direction of the irradiation solid angle. Or, if the size of the observation solid angle formed by the imaging device at the respective point on the inspection object is set sufficiently small, then, it becomes possible to set a threshold value for the tilt to be detected, in correspondence with the extension of the irradiation solid angle.

Further, as a still further embodiment of the aperture of the first shielding mask, if this aperture is composed of a shielding portion and an aperture portion coaxially, then, with appropriate setting of its width, for a partial tilt of the inspection object, detection can be made only for a certain predetermined tilt angle range; and with setting of its width by a required amount in a required direction, then, it becomes possible to provide its detection angle with anisotropy also. Or, if such inspection lighting is provided in multiple stages, then, classifying detection according to the degree of tilt of the surface will be made possible. Still further, if the first shielding mask is comprised of the liquid crystal member that allows electronic setting of its aperture, with dynamic switchover of its aperture pattern, a plurality of types of contrast information can be obtained, thus allowing more detailed classifying detection.

Moreover, if the second shielding mask is comprised of the liquid crystal member that allows electronic setting of its aperture, with dynamic switchover of its aperture pattern, the irradiation area of the inspection light can be changed. So, even when some inspection objects require different irradiation areas, the inspection light can be irradiated in accordance with each area, whereby a plurality of types of contrast information can be obtained.

Furthermore, if the surface light source is comprised of a combination of e.g. a color liquid crystal or the like and a white light source allowing dynamic change of emission light wavelength distribution, brightness distribution and polarized light state distribution of its irradiating face, then, it becomes possible to cope with an even greater variety of inspection objects.

Aside from the above, various modifications and combinations of the disclosed embodiments can be made as long as such modifications or combinations contradict the essence of the present invention.

REFERENCE SIGNS LIST

200: inspection system
100: inspection lighting system
1: surface light source
11: light emitting face
2: lens
4: half mirror
C: imaging device
L1: irradiation light path
L2: reflection/transmission light path
M1: first shielding mask
M2: second shielding mask
W: inspection object
P1: object-side focus of lens 2
P2: point having a same distance from lens 2 as P1
P3: point having a same distance from lens 2 as P1
P4: chosen point farther than object-side focus of lens 2
P5: chosen point farther than object-side focus of lens 2
IS: irradiation solid angle
OS: observation solid angle
RS1: solid angle of reflected light
RS2: solid angle of reflected light

The invention claimed is:

1. An inspection lighting device configured to irradiate inspection light onto an inspection object, the inspection lighting device adapted to an inspection system having an imaging device for imaging light reflected, transmitted or scattered by the inspection object, the inspection lighting device comprising:
a surface light source for emitting an inspection light;
a lens disposed between the surface light source and the inspection object and configured to form an irradiation solid angle for the inspection object by using light emitted from the surface light source as the inspection light to be irradiated onto the inspection object; and
a first shielding mask disposed between the surface light source and the lens and disposed at or ahead or behind a focus position of the lens, the first shielding mask being configured to form the irradiation solid angle of the inspection light irradiated onto at least one point on the inspection object by light shielding;

wherein at least a part of an area of the surface light source is a portion where an image is not formed on the inspection object by the lens, the inspection light being emitted to the inspection object from the surface light source including the part of the area, irrespective of a distance from the lens to the inspection object, with respect to an observation solid angle for the at least one point on the inspection object formed when the imaging device images light from the inspection object, a shape, a size or a tilt of the irradiation solid angle being settable concurrently at the at least one point and at any other point adjacent to the at least one point to obtain substantially the same change in contrast of the light reflected, transmitted or scattered from the at least one point and any other point in response to a tilt of a surface of the inspection object and a degree of non-mirror surface of the inspection object at the at least one point and at any other point adjacent to the at least one point.

2. The inspection lighting device according to claim 1, wherein the device further comprises a second shielding mask disposed between the first shielding mask and the surface light source and disposed adjacent position image-formed for the inspection object by the lens, the second shielding mask being capable of creating an irradiation area, an irradiation shape or an irradiation pattern of the inspection light for the inspection object as desired.

3. The inspection lighting device according to claim 2, wherein the device further comprises a half mirror disposed between the lens and the inspection object and provided for changing an irradiation direction of an inspection light and also allowing transmission of light from the inspection object to be image-captured by the imaging device, and an optical axis of the irradiation solid angle of the inspection light for the respective point on the inspection object is rendered into approximate agreement with an optical axis of the observation solid angle of the imaging device for the respective point on the inspection object.

4. An inspection system using the inspection lighting device according to claim 2 and having an imaging device for imaging light reflected, transmitted or scattered by the inspection object, wherein for the inspection light irradiated by the inspection lighting device onto the inspection object, a shape, a size or a tilt of the irradiation solid angle for the respective point on the inspection object is set, based on a shape, a size or a tilt of an observation solid angle of the imaging device for respective point on the inspection object.

5. The inspection lighting device according to claim 1, wherein the device further comprises a half mirror disposed between the lens and the inspection object and provided for changing an irradiation direction of an inspection light and also allowing transmission of light from the inspection object to be image-captured by the imaging device, and an optical axis of the irradiation solid angle of the inspection light for the respective point on the inspection object is rendered into approximate agreement with an optical axis of the observation solid angle of the imaging device for the respective point on the inspection object.

6. An inspection system using the inspection lighting device according to claim 5 and having an imaging device for imaging light reflected, transmitted or scattered by the inspection object, wherein for the inspection light irradiated by the inspection lighting device onto the inspection object, a shape, a size or a tilt of the irradiation solid angle for the respective point on the inspection object is set, based on a shape, a size or a tilt of an observation solid angle of the imaging device for respective point on the inspection object.

7. An inspection system using the inspection lighting device according to claim 1 and having an imaging device for imaging light reflected, transmitted or scattered by the inspection object, wherein for the inspection light irradiated by the inspection lighting device onto the inspection object, a shape, a size or a tilt of the irradiation solid angle for the respective point on the inspection object is set, based on a shape, a size or a tilt of an observation solid angle of the imaging device for respective point on the inspection object.

8. The inspection lighting device according to claim 1, wherein the entire area of the surface light source is disposed at the position different from the position image-formed on the inspection object by the lens, irrespective of a distance from the lens to the inspection object.

9. The inspection lighting device according to claim 1, additionally comprising a second shielding mask disposed between the first shielding mask and the surface light source and disposed adjacent a position image-formed for the inspection object by the lens, the second shielding mask being mounted in a manner to advance or retract along the irradiation path.

10. The inspection lighting device according to claim 1, wherein the same or a constant irradiation solid angle is achieved in any point of the inspection object.

* * * * *